(12) United States Patent
Abboud et al.

(10) Patent No.: US 9,039,712 B2
(45) Date of Patent: May 26, 2015

(54) SHAPE MODIFICATION SYSTEM FOR A COOLING CHAMBER OF A MEDICAL DEVICE

(75) Inventors: Marwan Abboud, Pierrefonds (CA); Dan Wittenberger, L'Ile Bizard (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 2015 days.

(21) Appl. No.: 11/476,408

(22) Filed: Jun. 28, 2006

(65) Prior Publication Data

US 2008/0004652 A1    Jan. 3, 2008

(51) Int. Cl.
*A61F 11/00* (2006.01)
*A61M 25/10* (2013.01)

(52) U.S. Cl.
CPC ... *A61M 25/1018* (2013.01); *A61M 2025/1068* (2013.01)

(58) Field of Classification Search
USPC ......... 606/192, 194, 108, 191, 198; 623/1.11; 604/27, 48
See application file for complete search history.

(56) References Cited

U.S. PATENT DOCUMENTS

| | | | |
|---|---|---|---|
| 4,813,934 A | 3/1989 | Engelson et al. | |
| 4,846,174 A | 7/1989 | Willard et al. | |
| 4,968,300 A * | 11/1990 | Moutafis et al. | 604/103.07 |
| 5,397,308 A * | 3/1995 | Ellis et al. | 604/100.03 |
| 5,423,755 A * | 6/1995 | Kesten et al. | 604/103.09 |
| 5,928,193 A | 7/1999 | Campbell | |
| 6,780,183 B2 * | 8/2004 | Jimenez et al. | 606/41 |
| 7,097,643 B2 | 8/2006 | Cornelius et al. | |
| 2003/0158516 A1 | 8/2003 | Wholey et al. | |
| 2007/0233222 A1 * | 10/2007 | Roeder et al. | 623/1.11 |

* cited by examiner

*Primary Examiner* — Victor Nguyen
*Assistant Examiner* — Kevin Everage
(74) *Attorney, Agent, or Firm* — Christopher & Weisberg, P.A.

(57) ABSTRACT

The present invention provides a medical device having an catheter body defining proximal and distal portions, and a guidewire lumen at least partially disposed within and movable within the catheter body. The medical device may include an expandable element defining a proximal end and a distal end, wherein the proximal end is coupled to the distal portion of the catheter body and the distal end is coupled to the guidewire lumen. In addition, an actuator element may be coupled to the guidewire lumen for longitudinal movement thereof, and a tensioning element may further be coupled to the guidewire lumen to bias the guidewire lumen and/or the expandable element towards a particular geometric configuration.

19 Claims, 5 Drawing Sheets

SHAPE MODIFICATION SYSTEM FOR A COOLING CHAMBER OF A MEDICAL DEVICE

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for modifying and controlling forces applied to a portion of a medical device, and more particularly, to a method and system for tensioning and/or varying the shape of an expandable element.

BACKGROUND OF THE INVENTION

Numerous procedures involving catheters and other minimally invasive devices may be performed to provide a wide variety of treatments, such as ablation, angioplasty, dilation or the like. Prior to insertion into a vessel and/or placement near a particular tissue region, the balloon is typically in a deflated state, and may include a number of folds that reduce the cross-sectional area of the balloon to ease insertion and/or placement. During a particular procedure, the balloon may be transitioned between inflated and deflated states in order to provide the desired affect. Such cycling can cause portions of the internal components of the catheter to experience axial movement. Moreover, when the balloon is deflated subsequent to a desired inflation, it may not necessarily deflate into its original, folded state occurring prior to use. Rather the balloon may bunch up or otherwise improperly deflate, causing the deflated balloon to have a larger than desirable radius, which may cause complications during the extraction and/or repositioning of the medical device.

In addition, when a balloon is employed, it often must be manufactured or constructed to have a particular shape or dimension for a specific application, and as such, any given catheter with a balloon may be limited to use in situations where the fixed dimensions of the balloon are appropriate. For example, a balloon may have a fixed radius in an inflated state, making it only suitable for a procedure requiring such a dimension or where a particular vasculature may accommodate that radius. As such, multiple catheters having varying fixed dimensions may be needed to successfully perform a desired treatment.

Accordingly, in light of the above limitations, it would be desirable to provide a medical device in which the balloon could be caused to deflate into its original, uninflated and folded orientation for ease of removal and/or repositioning. Moreover, it would be desirable to provide a medical device having an expandable element, such as a balloon, in which the particular size, shape, and/or dimensions of the balloon may be controlled and modified during use.

SUMMARY OF THE INVENTION

The present invention advantageously provides a medical device in which an expandable element could be caused to deflate into its original, uninflated and folded orientation for ease of removal and/or repositioning. Moreover, the medical device of the present invention may include an expandable element, such as a balloon, in which the particular size, shape, and/or dimensions of the balloon may be controlled and modified during use.

The medical device may include an elongate body defining a proximal portion, a distal portion, and a fluid injection lumen, and a handle portion coupled to the proximal portion of the elongate body. A guidewire lumen may be at least partially disposed within the elongate body, wherein the guidewire lumen includes a proximal end and a distal end. The medical device may further include an expandable element coupled to the elongate body, with the expandable element defining a proximal end and a distal end, such that the proximal end may be coupled to the distal portion of the catheter body, and the distal end being coupled to either the tip portion or the guidewire lumen. The expandable element may also be in fluid communication with the fluid injection lumen.

The medical device may further include a tensioning element coupled to a portion of the guidewire lumen and/or the handle element. The tensioning element may provide a biasing force that predisposes or urges a portion of the guidewire lumen into a particular configuration. An actuator element may be movably coupled to the proximal portion of the elongate body and/or the handle, and further coupled to the proximal portion of the guidewire lumen to allow manual manipulation and control of the guidewire lumen and related components. Moreover, the medical device of the present invention may further include a size detection element for determining and/or indicating a particular dimension of the expandable element at any given time during a procedure in which the medical device is in use.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
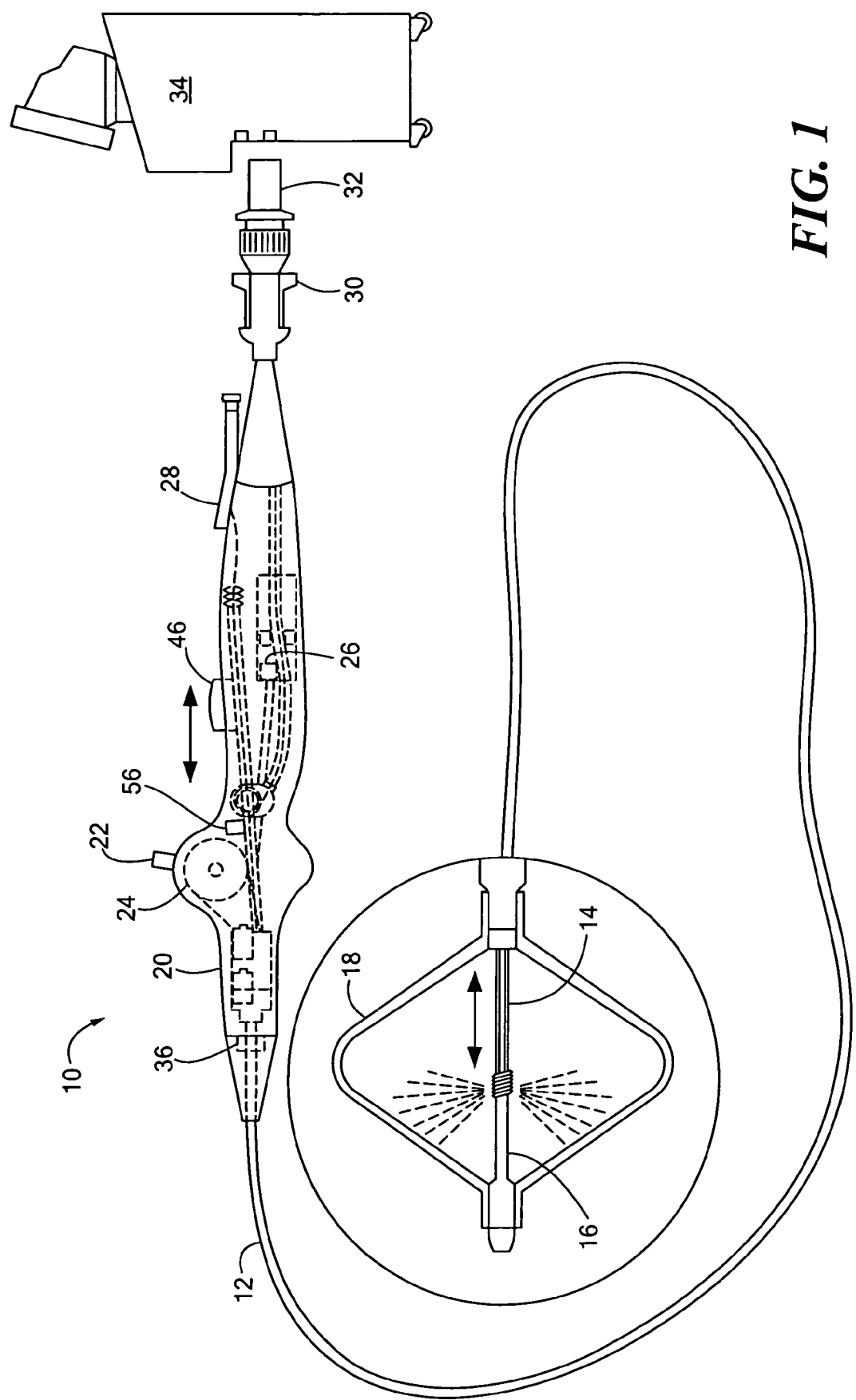
FIG. 1 illustrates an embodiment of a medical device in accordance with the present invention.
Figure 2:
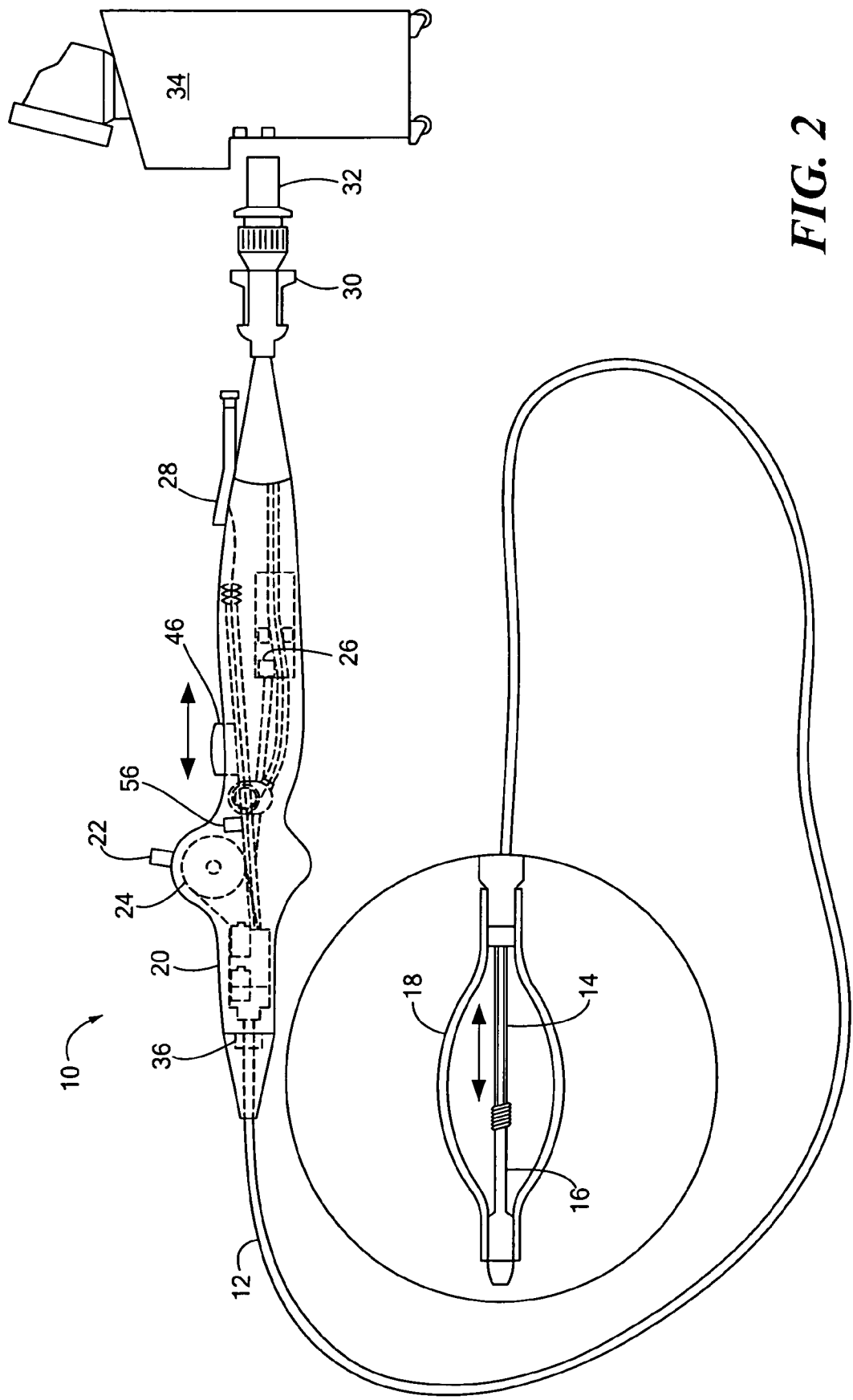
FIG. 2 shows an embodiment of a medical device in accordance with the present invention.

Now referring to FIGS. 1 and 2, an embodiment of the present invention provides a medical device, generally designated as 10. The medical device 10 may include an elongate body 12, such as a catheter. The elongate body 12 may define a proximal portion and a distal portion, and may further include one or more lumens may disposed within the elongate body 12 thereby providing mechanical, electrical, and/or fluid communication between the proximal portion of the elongate body 12 and the distal portion of the elongate body 12. For example, the elongate body 12 may include an injection lumen 14 and an exhaust lumen defining a fluid flow path therethrough. In addition, the elongate body 12 may include a guidewire lumen 16 movably disposed within and/or extending along at least a portion of the length of the elongate body 12 for over-the-wire applications. The guidewire lumen 16 may define a proximal end and a distal end, and the guidewire lumen 16 may be movably disposed within the elongate body 12 such that the distal end of the guidewire lumen 16 extends beyond and out of the distal portion of the elongate body 12.

The medical device 10 of the present invention may further include an expandable element 18 at least partially disposed on the elongate catheter body. The expandable element 18 may include a balloon or other expandable structure, which may define a proximal end coupled to the distal portion of the elongate body 12 of the catheter, while further defining a distal end coupled to the distal end of the guidewire lumen 16. As such, due to the movable nature of the guidewire lumen 16 about the elongate body 12, any axial and/or longitudinal movement of the guidewire lumen 16 may act to tension or loosen the expandable element 18, i.e., extend or retract the expandable element 18 from a lengthened state to a shortened state during deflation or inflation, respectively. In addition, the expandable element 18 may have any of a myriad of shapes, and may further include one or more material layers providing for puncture resistance, radiopacity, or the like. The expandable element 18 may be in communication with the fluid injection and exhaust lumens of the medical device 10 as described above, i.e., a fluid flow path may provide an inflation fluid, such as a cryogenic fluid or the like, to the interior of the expandable element 18. In addition, a sheath (not shown) may be provided which is slidably positionable about at least a portion of the elongate body 12 of the medical device 10 and/or the expandable element 18.

The medical device 10 may include a handle element 20 coupled to the proximal portion of the elongate body 12, where the handle may include an element such as a lever or knob 22 for manipulating the catheter body and/or additional components of the medical device 10. For example, a pull wire with a proximal end and a distal end may have its distal end anchored to the elongate body 12 at or near the distal end. The proximal end of the pull wire may be anchored to an element such as a cam 24 in communication with and responsive to the lever. The handle 20 can further include circuitry for identification and/or use in controlling of the medical device 10 or another component of the system. For example, the handle may include one or more pressure sensors 26 to monitor the fluid pressure within the medical device 10. Additionally, the handle may be provided with a fitting 28 for receiving a guidewire that may be passed into the guidewire lumen 16, which may be partially disposed within the elongate body 12.

The handle may also include connectors that are matable directly to a fluid supply/exhaust and control unit or indirectly by way of one or more umbilicals for providing fluid communication with the second elongate body 12. For example, the handle may be provided with a first connector 30 that is matable with a co-axial fluid umbilical (not shown) and a second connector 32 that is matable with an electrical umbilical (not shown) that can further include an accessory box (not shown). In an exemplary system, a fluid supply and exhaust, as well as various control mechanisms for the system may be housed in a single console 34. In addition to providing an exhaust function for the catheter fluid supply, the console 34 may also recover and/or re-circulate fluid delivered to the handle 20 and the elongate body 12 of the medical device 10.

A vacuum pump in the console may create a low-pressure environment in one or more conduits within the catheter body so that fluid is drawn into the conduit(s), away from the expandable element 18, and towards the proximal end of the catheter.

Figure 3:
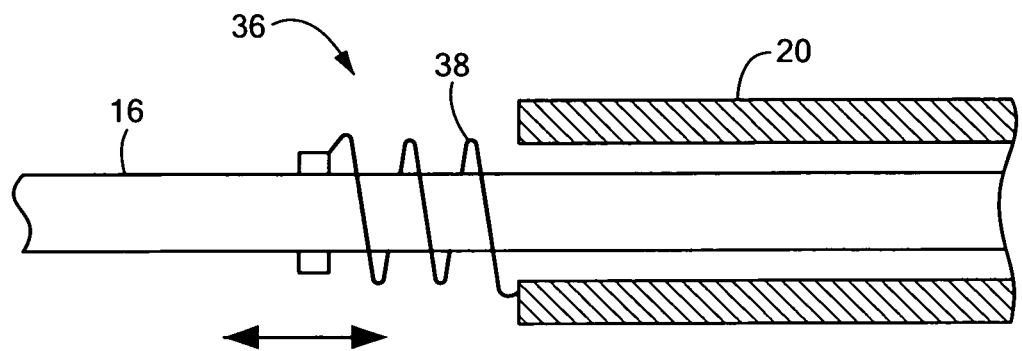
FIG. 3 depicts an embodiment of a tensioning element in accordance with the present invention.
Figure 4:
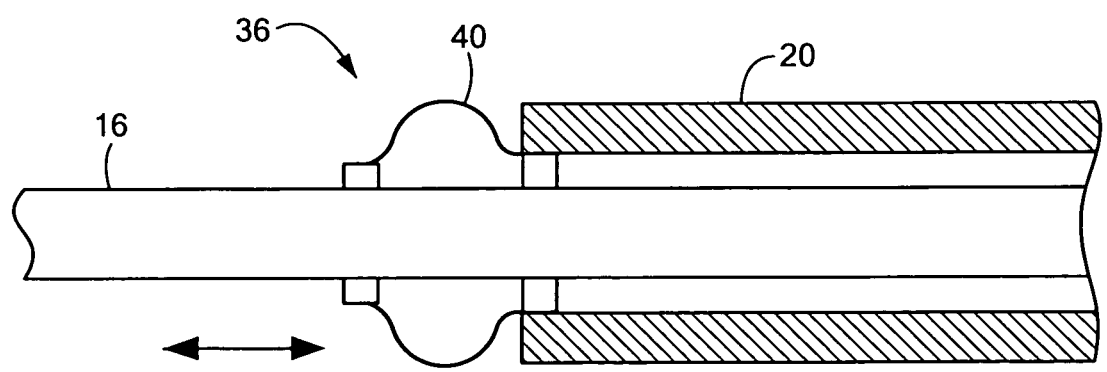
FIG. 4 illustrates an embodiment of a tensioning element in accordance with the present invention.
Figure 5:
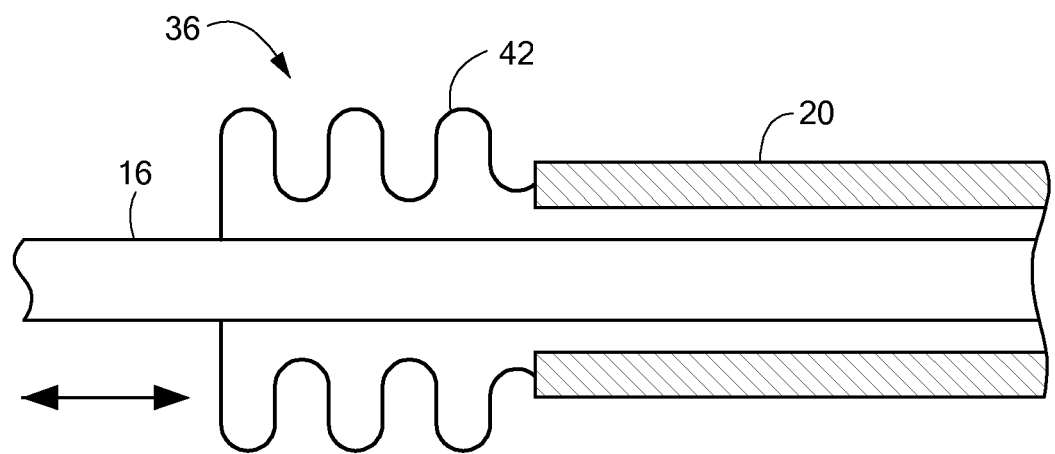
FIG. 5 shows an embodiment of a tensioning element in accordance with the present invention.
Figure 6:
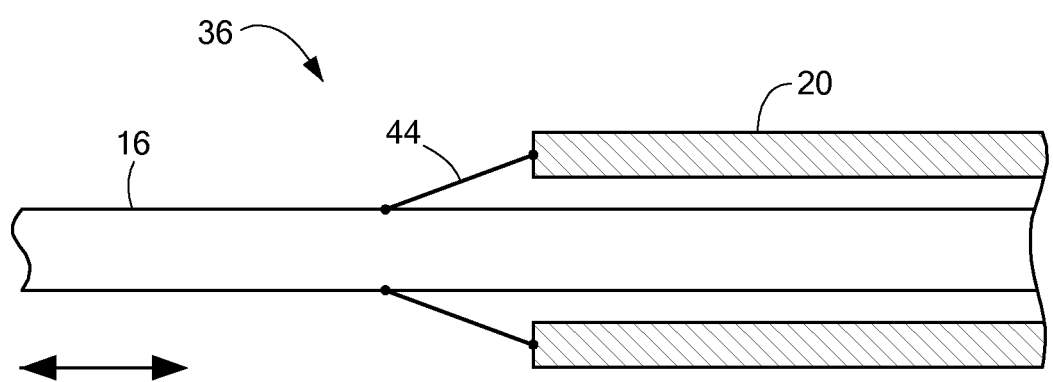
FIG. 6 depicts an embodiment of a tensioning element in accordance with the present invention.

The medical device 10 of the present invention may include a tensioning element 36 coupled to a portion of the guidewire lumen 16 and/or the handle element 20. The tensioning element 36 may provide a biasing force that predisposes or urges a portion of the guidewire lumen 16 to extend away from the handle element 20, and to further protrude a greater distance from the distal end of the elongate body 12. For example, as shown in FIG. 3, the tensioning element 36 may include a spring 38 having first and second ends, with the first end coupled to a portion of the guidewire lumen 16, and the second end coupled to the handle element 20. In a first state, the spring 38 provides a resistive force that biases the guidewire lumen 16 in a direction away form the handle element 20. During use of the medical device 10, the expandable element 18 may be inflated, causing the expandable element 18 to expand and thereby causing the guidewire lumen 16 to retract somewhat in the direction of the handle 20, i.e., the force resulting from the expansion of the expandable element 18 overcomes and/or dominates the force provided by the spring 38. When the expandable element 18 begins to deflate, the bias provided by the spring 38 then shifts the guidewire lumen 16 away from the handle 20, thereby placing tension on the expandable element 18. Similar to the operation of the spring 38, additional and/or alternative structures may be employed to provide a biasing force that is ultimately communicated to the expandable element 18. As shown in FIGS. 4-6, for instance, a compliant balloon 40 could be disposed about the guidewire lumen 16 and/or the handle to provide the desired bias, or a bellow structure 42 could be integrated into the medical device 10. In addition, an elastic member 44 could be coupled to handle and/or guidewire lumen 16 to counter the forces experienced during inflation of the expandable element 18.

Referring again to FIGS. 1 and 2, in addition, the medical device 10 of the present invention may include an actuator element 46 that is movably coupled to the proximal portion of the elongate body 12 and/or the handle 20, and further coupled to the proximal portion of the guidewire lumen 16. Accordingly, manipulating the actuator element 46 in a longitudinal direction may cause the guidewire lumen 16 to slide towards either of the proximal or distal portions of the elongate body 12. As a portion of the expandable element 18 may be coupled to the guidewire lumen 16, manipulation of the actuator element 46 may further cause the expandable element 18 to be tensioned or loosened, depending on the direction of movement of the actuator element 46, and thus, the guidewire lumen 16. Accordingly, the actuator element 46 may be used to provide tension on the expandable element 18 during a particular duration of use of the medical device 10, such as during a deflation sequence, for example. In addition, the actuator element 46 may be used in controlling a particular geometric configuration and/or dimension of the expandable element 18, i.e., the actuator element 46 may exert a tensile force on the expandable element 18 to provide for an elongated, cylindrical shape. Subsequently, the actuator element 46 may be retracted to allow the expandable element 18 to assume a spherical shape having a larger radius than that of the elongated shape experienced under tension.

Figure 7:
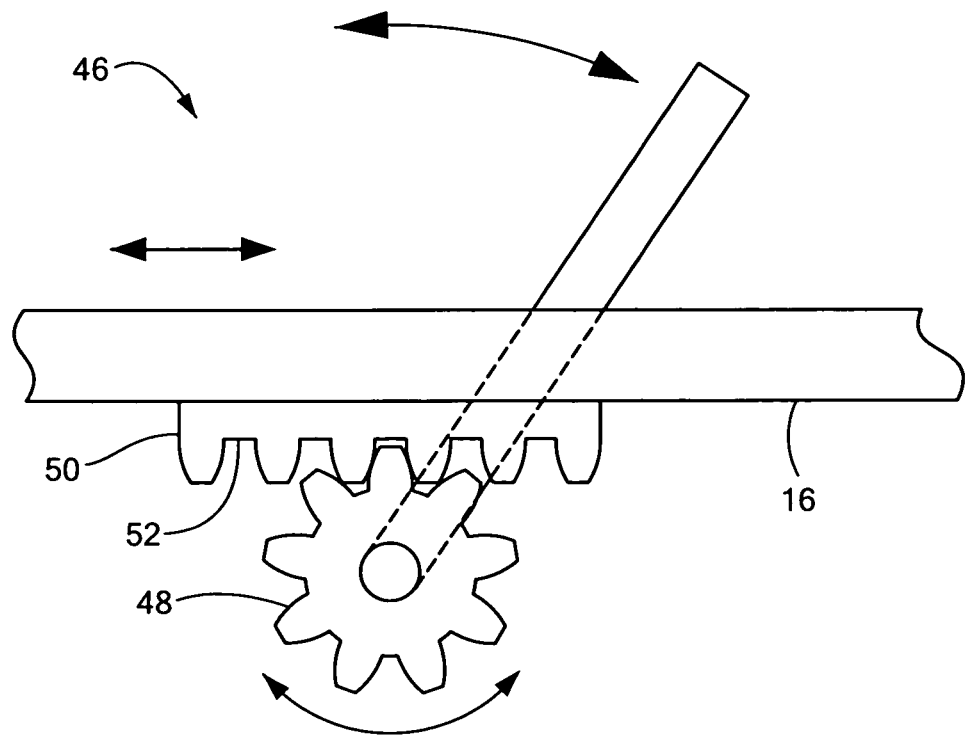
FIG. 7 illustrates an embodiment of an actuator element in accordance with the present invention.
Figure 8:
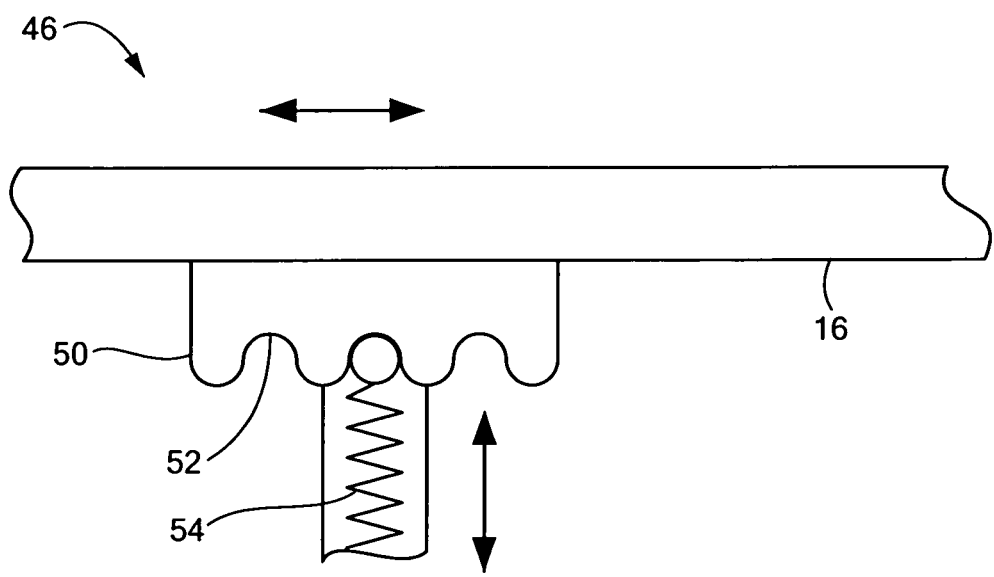
FIG. 8 shows an embodiment of an actuator element in accordance with the present invention.

The actuator element 46 may include a thumb-slide, a push-button, a rotating lever, or other mechanical structure for providing a movable coupling to the elongate body 12, the handle, and/or the guidewire lumen 16. Moreover, the actuator element 46 may be movably coupled to the handle such that the actuator element 46 is movable into individual, distinct positions, and is able to be releasably secured in any one of the distinct positions. As shown in FIGS. 7 and 8, for example, the actuator element 46 may include a gear 48 having a plurality of protrusions, and the handle element 20 and/or guidewire lumen 16 may include a track 50 having a plurality of indentations 52. The gear 48 may be rotated to provide for longitudinal advancement or retraction such that the plurality of protrusions sequentially engage the plurality of indentations 52 on the track. Similarly, the actuator element 46 may include a spring-loaded ball 54 which is biased towards engaging the plurality of indentations 52 of the track 50. To move the actuator element 46, the biasing force of the spring may be overcome to allow the actuator element 46, and thus the guidewire lumen, to be advanced or retracted in a controlled manner along the multiple positions provided by the indentations of the track. The medical device 10 may further include indicia located on the handle element 20 in proximity to each distinct position in which the actuator element 46 may be located, where the indicia may directly correspond to a given dimension and/or shape the expandable element 18 resulting from the particular position of the actuator element 46.

As shown in FIGS. 1 and 2, the medical device 10 of the present invention may further include a size detection element 56 for determining and/or indicating a particular dimension of the expandable element 18 at any given time during a procedure in which the medical device 10 is in use. The size detection element 56 may include a component capable of providing a resistance, impedance, or capacitance measurement that may be correlated to a particular state of the expandable element 18. For example, the size detection element 56 may include a potentiometer coupled to the handle element 20, the guidewire lumen 16 and/or the actuator element 46. When the actuator element 46, and thus the guidewire lumen 16 and the expandable element 18, are in a first position, a resistance, impedance, or capacitance measurement may be indicated by the potentiometer of the size detection element. This measurement may be correlated to a particular dimension, i.e., length, radius, etc., of the expandable element 18 (it is understood that the medical device 10, expandable element 18, and size detection element 56 may need to be initially calibrated or measured in order to determine the relationship between the measurement taken by the size detection element and the corresponding dimension of the expandable element 18). Subsequently, the actuator element 46, guidewire, and expandable element 18 may be moved into a second position and/or state. This movement causes a change in the resistive, capacitive, or impedance characteristics of the potentiometer. A corresponding resistance, impedance, or capacitance measurement may again be indicated by the potentiometer of the size detection element 56 to provide information regarding the particular dimensions of the expandable element 18 in the second position. The information regarding the particular dimensions and/or state of the expandable element 18 may be relayed to the control console 34 and used to determine desirable flow rates, temperatures, etc. for appropriate operation of the medical device 10.

In an exemplary use, an embodiment of the medical device 10 of the present invention may be employed in a particular surgical procedure in which it will be desirable to both inflate and subsequently deflate the expandable element 18. Accordingly, the distal portion of the elongate body 12 of the medical device 10 may be positioned in proximity to a desired tissue region. The positioning may include moving a portion of the elongate body 12 and the expandable element 18 out of a sheath or similar introducer element. At this stage, the expandable element 18 is presumably uninflated, and maintains a folded position about the elongate body 12 and guidewire lumen 16, thereby providing a minimized cross-section for ease of insertion and positioning of the medical device 10. Once the desired position has been attained, the actuator element 46 may be positioned to correspond to a desired size and/or dimension of the expandable element 18. In addition, the position of the guidewire lumen 16 and thus the expandable element 18 may be dictated in part by the tensioning element 36. Subsequently, the expandable element 18 may be inflated, and the particular size and/or dimensions of the expandable element 18 may be monitored through the size detection element 56. Once inflated to the preferred size, a desired procedure may be performed by the inflated expandable element 18. Such procedures may include ablation, dilation, or the like.

When inflation of the expandable element 18 is no longer needed, the expandable element 18 may begin to be deflated. During the deflation, tension may be placed on the guidewire lumen 16, and thus the expandable element 18, by either the biasing force of the tensioning element 36, or by a manual force applied to the actuator element 46, or by a combination thereof. The tension experienced by the expandable element 18 during deflation may cause the expandable element 18 to extend longitudinally, which aids the expandable element 18 in resuming the appropriate folded configuration experienced by the expandable element 18 prior to inflation. As the expandable element 18 resumes a minimized cross-section, the medical device 10 may be repositioned and/or extracted with ease, without the complications arising from a deflated expandable element 18 having an enlarged volume and/or cross-section due to improper folding or bunching.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   a catheter body defining a proximal portion and a distal portion;
   a guidewire lumen at least partially disposed within and movable within the catheter body, wherein the guidewire lumen includes a proximal end and a distal end, the distal end being disposed outside the catheter body;
   a tensioning element coupled to the guidewire lumen wherein the tensioning element biases the guidewire lumen towards a pre-determined longitudinal position; and
   an expandable element defining a proximal end and a distal end, wherein the proximal end is coupled to the distal portion of the catheter body and the distal end is coupled to the guidewire lumen.

2. The medical device according to claim 1, further comprising an actuator element coupled to the guidewire lumen for manipulation of longitudinal movement thereof.

3. The medical device according to claim 2, further comprising a handle element coupled to the proximal portion of the catheter body.

4. The medical device according to claim 3, wherein the actuator element is movably coupled to the handle element.

5. The medical device according to claim 4, wherein the actuator element is releasably securable in a plurality of discrete positions on the handle element.

6. The medical device according to claim 4, wherein the handle element includes a plurality of indentations, and wherein the actuator element includes a plurality of protrusions engageable with the plurality of indentations.

7. The medical device according to claim 4, wherein the handle element includes a plurality of indentations, and wherein the actuator element includes a biased element engageable with the plurality of indentations.

8. The medical device according to claim 1, further comprising a size detection element coupled to the guidewire lumen.

9. The medical device according to claim 8, wherein the size detection element includes one of a resistance element, a capacitance element, and an impedance element.

10. The medical device according to claim 1, wherein the tensioning element includes a spring.

11. The medical device according to claim 1, wherein the tensioning element includes an elastic member.

12. The medical device according to claim 1, further comprising a handle element coupled to the proximal portion of the catheter body.

13. The medical device according to claim 12, wherein the tensioning element is further coupled to the handle element.

14. A medical device, comprising:
   a catheter body defining a proximal portion and a distal portion;
   a guidewire lumen at least partially disposed within and movable within the catheter body, wherein the guidewire lumen includes a proximal end and a distal end, the distal end being disposed outside the catheter body;
   an expandable element defining a proximal end and a distal end, wherein the proximal end is coupled to the distal portion of the catheter body and the distal end is coupled to the guidewire lumen; and
   a tensioning element coupled to the guidewire lumen wherein the tensioning element biases the guidewire lumen towards a pre-determined configuration, wherein the tensioning element includes a balloon.

15. A medical device, comprising:
   a catheter body defining a proximal portion and a distal portion;
   a guidewire lumen at least partially movably disposed within the catheter body, wherein the guidewire lumen includes a proximal end and a distal end, the distal end being disposed outside the catheter body;
   an expandable element defining a proximal end and a distal end, wherein the proximal end is coupled to the distal portion of the catheter body and the distal end is coupled to the guidewire lumen;
   a tensioning element coupled to the guidewire lumen, wherein the tensioning element biases the guidewire lumen towards a pre-determined longitudinal configuration, such that when the expandable element is expanded, a force applied by the expandable element on the guidewire lumen at least partially overcomes the bias applied by the tensioning element; and
   an actuator element coupled to the guidewire lumen for manipulation of longitudinal movement thereof.

16. The medical device according to claim 15, further comprising a handle element coupled to the proximal portion of the catheter body.

17. The medical device according to claim 16, wherein the tensioning element and the actuator element are further coupled to the handle element.

18. The medical device according to claim 15, further comprising a size detection element coupled to the guidewire lumen.

19. The medical device according to claim 18, wherein the size detection element includes one of a resistance element, a capacitance element, and an impedance element.

\* \* \* \* \*